(12) United States Patent
Kurkal-Siebert et al.

(10) Patent No.: US 9,949,475 B2
(45) Date of Patent: Apr. 24, 2018

(54) COMPOSITION COMPRISING ACTIVE INGREDIENT, OIL AND IONIC LIQUID

(76) Inventors: Vandana Kurkal-Siebert, Heidelberg (DE); Ann-Kathrin Marguerre, Heidelberg (DE); Daher Michael Badine, Mannheim (DE); Ulrike Troppmann, Schifferstadt (DE); Ansgar Schäfer, Karlsruhe (DE); Sebastian Koltzenburg, Neustadt (DE); Karolin Geyer, Mannheim (DE); Murat Cetinkaya, Heidelberg (DE); Eduard Schreiner, Bochum (DE); Nikolaus Nestle, Heidelberg (DE); Andreas Hopf, Neustadt (DE); Ingolf Hennig, Neulussheim (DE); Karsten Seidel, Mannheim (DE); Jürgen Mertes, Ludwigshafen (DE)

(*) Notice: Subject to any disclaimer, the term of this patent is extended or adjusted under 35 U.S.C. 154(b) by 9 days.

(21) Appl. No.: 14/238,928

(22) PCT Filed: Aug. 14, 2012

(86) PCT No.: PCT/EP2012/065912
§ 371 (c)(1),
(2), (4) Date: Jun. 12, 2014

(87) PCT Pub. No.: WO2013/024099
PCT Pub. Date: Feb. 21, 2013

(65) Prior Publication Data
US 2015/0004109 A1 Jan. 1, 2015

Related U.S. Application Data

(60) Provisional application No. 61/523,858, filed on Aug. 16, 2011.

(30) Foreign Application Priority Data

Aug. 16, 2011 (EP) ..................................... 11177649

(51) Int. Cl.
| | |
|---|---|
| *A01N 25/30* | (2006.01) |
| *A01N 43/56* | (2006.01) |
| *A61K 8/37* | (2006.01) |
| *A61K 8/41* | (2006.01) |
| *A61K 8/49* | (2006.01) |
| *A61Q 17/04* | (2006.01) |
| *A01N 33/04* | (2006.01) |
| *A01N 33/06* | (2006.01) |
| *A01N 25/02* | (2006.01) |
| *A61Q 17/00* | (2006.01) |

(52) U.S. Cl.
CPC ............ *A01N 25/30* (2013.01); *A01N 25/02* (2013.01); *A01N 33/04* (2013.01); *A01N 33/06* (2013.01); *A01N 43/56* (2013.01); *A61K 8/37* (2013.01); *A61K 8/416* (2013.01); *A61K 8/4946* (2013.01); *A61K 8/4966* (2013.01); *A61Q 17/00* (2013.01); *A61Q 17/04* (2013.01); *A01N 2300/00* (2013.01); *A61K 2800/49* (2013.01); *A61K 2800/591* (2013.01)

(58) Field of Classification Search
None
See application file for complete search history.

(56) References Cited

U.S. PATENT DOCUMENTS

| | | | |
|---|---|---|---|
| 5,236,698 A | 8/1993 | Richard et al. | |
| 5,332,568 A | 7/1994 | Raspanti | |
| 5,338,539 A | 8/1994 | Raspanti | |
| 5,518,713 A | 5/1996 | Raspanti | |
| 5,520,906 A | 5/1996 | Stein et al. | |
| 5,601,811 A | 2/1997 | Gallagher et al. | |
| 2002/0131939 A1* | 9/2002 | Djerassi ................. | A61K 8/342 424/59 |
| 2003/0125222 A1 | 7/2003 | Jahns et al. | |
| 2006/0166856 A1 | 7/2006 | Petrat et al. | |
| 2008/0070966 A1* | 3/2008 | Elder ..................... | A01N 43/50 514/385 |
| 2010/0137175 A1 | 6/2010 | Kunz et al. | |

FOREIGN PATENT DOCUMENTS

| | | |
|---|---|---|
| EP | 507691 A1 | 10/1992 |
| EP | 517104 A1 | 12/1992 |
| EP | 0 570 838 A1 | 11/1993 |
| EP | 582189 A2 | 2/1994 |
| EP | 613893 A1 | 9/1994 |

(Continued)

OTHER PUBLICATIONS https://en.wikipedia.org/wiki/Bergamot_essential_oil.*
https://en.wikipedia.org/wiki/Cod_liver_oil.*
Brosnan et al. "Sodium Chloride Salt Applications Provide Effective Control of Sourgrass (*Paspalum conjugatum*) in Seashore Paspalum Turf", Weed Technology 23(2):251-256 2009.*
International Search Report for PCT/EP2012/065912 dated Sep. 20, 2012.
Rogers et al., "Ionic Liquid—Solvents of the Future?", Science, American Association for the Advancement of Science, vol. 302, pp. 792-793, Oct. 31, 2003.

(Continued)

*Primary Examiner* — James W Rogers
(74) *Attorney, Agent, or Firm* — Drinker Biddle & Reath LLP

(57) ABSTRACT

The present invention relates to a liquid composition comprising A) an organic active ingredient which is sparingly water-soluble and sparingly oil-soluble, in dissolved form, B) an oil which is soluble in water at 20° C. to at most 20 g/l, and C) an ionic liquid comprising a cation and an anion as described below. Also provided is a process for the preparation of the liquid composition, where the active ingredient, the oil and the ionic liquid are brought into contact; and also the use of the ionic liquid for increasing the solubility of the active ingredient in an oil.

17 Claims, No Drawings

(56) References Cited

FOREIGN PATENT DOCUMENTS

| EP | 709080 A1 | 5/1996 |
|---|---|---|
| WO | WO-93/17002 A1 | 9/1993 |
| WO | WO-97/00851 A1 | 1/1997 |
| WO | WO-01/49817 A2 | 7/2001 |
| WO | WO-2004035018 A2 | 4/2004 |
| WO | WO-2007144286 A1 | 12/2007 |
| WO | WO-2008135482 A2 | 11/2008 |

\* cited by examiner

COMPOSITION COMPRISING ACTIVE INGREDIENT, OIL AND IONIC LIQUID

This application is a national stage application (under 35 U.S.C. § 371) of PCT/EP2012/065912, filed Aug. 14, 2012, which claims benefit of U.S. Provisional Application No. 61/523,858, filed Aug. 16, 2011 and European Application No. 11177649.8, filed Aug. 16, 2011.

The present invention relates to a liquid composition comprising A) an organic active ingredient which is sparingly water-soluble and sparingly oil-soluble, in dissolved form, B) an oil which is soluble in water at 20° C. to at most 20 g/l, and C) an ionic liquid comprising a cation and an anion, as described below. Also provided is a process for the preparation of the liquid composition, where the active ingredient, the oil and the ionic liquid are brought into contact; and also the use of the ionic liquid for increasing the solubility of the active ingredient in an oil. Combinations of preferred features with other preferred features are comprised by the present invention.

Composition comprising active ingredient, ionic liquid and oil are generally known:

WO 2007/144286 describes an antimicrobial composition comprising an ionic liquid which comprises, as cation, an N-carboxyalkylimidazolium radical and, as anion, an alkylsulfonate, alkyl phosphate or alkyl carboxylate. The composition can comprise hydrocarbon oils or antimicrobial active ingredients.

Disadvantages of the known compositions comprising active ingredient, ionic liquid and oil are, inter alia, that the ionic liquid can only be prepared with complexity, that they have a low agrochemical effect, that the addition of nonionic or anionic surfactants is necessary, that no high concentrations of active ingredient can be brought into solution, that the composition is relatively toxic; that the active ingredient could be chemically degraded by the ionic liquid. An object of the present invention was to overcome these disadvantages.

The object was achieved by a liquid composition comprising
A) an organic active ingredient which is sparingly water-soluble and sparingly oil-soluble, in dissolved form,
B) an oil which is soluble in water at 20° C. to at most 20 g/l, and
C) an ionic liquid comprising a cation and an anion, where the cation comprises an ammonium of the formula (I)

$$N^+R^1R^2R^3R^4 \quad (I)$$

and $R^1$, $R^2$, $R^3$ and $R^4$, independently of one another, are alkyl radicals which may be substituted with heterofunctional groups, and which can form aliphatic ring systems with one another;
an imidazolium of the formula (II)

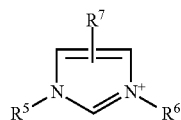

(II)

and $R^5$ is hydrogen or alkyl, $R^6$ is alkyl, and $R^7$ is hydrogen or alkyl,
an N-substituted pyridinium derivative;
an N,N'-disubstituted pyrazolium derivative; or
a guanidinium derivative.

The active ingredient is an organic active ingredient. Besides the at least one organic active ingredient, further active ingredients may also be present. The further active ingredients may be organic or inorganic.

The composition can comprise one or more different active ingredients, such as agrochemical, cosmetic, or pharmaceutical active ingredients. In a preferred form, active ingredients are agrochemical active ingredients. In a further preferred form, active ingredients are cosmetic active ingredients. In a further preferred form, active ingredients are pharmaceutical active ingredients. In another preferred form, active ingredients are agrochemical active ingredients or UV absorbers. In another form, fragrances and aroma substances are excluded from active ingredients.

The active ingredient is sparingly water-soluble. It is in most cases soluble in water at 20° C. to at most 10 g/L, preferably to at most 3 g/l, and in particular to at most 0.5 g/l.

The active ingredient is sparingly oil-soluble. It is in most cases soluble in dibutyl adipate (such as Cetiol® B) at 20° C. to at most 10% by weight, preferably to at most 5% by weight, and in particular to at most 3% by weight.

The active ingredient, in particular at least one active ingredient, is present in dissolved form in the composition. The composition can also comprise further active ingredients, which may be present in dissolved or undissolved form.

Examples of pharmaceutical active ingredients which may be mentioned here are: benzodiazepines, antihypertensives, vitamins, cytostatics, in particular taxol, anesthetics, neuroleptics, antidepressants, antiviral agents, such as, for example, anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutic agents, psychopharmacological agents, agents for treating Parkinson's disease and other antihyperkinetic agents, ophthalmics, neuropathy preparations, calcium metabolism regulators, muscle relaxants, narcotics, lipid-lowering agents, hepatic therapeutic agents, coronary agents, cardiacs, immunotherapeutics, regulatory peptides and their inhibitors, hypnotics, sedatives, gynecological agents, gout remedies, fibrinolytic agents, enzyme preparations and transport proteins, enzyme inhibitors, emetics, circulation-promoting agents, diuretics, diagnostics, corticoids, cholinergics, bile duct therapeutics, antiasthmatics, broncholytics, beta receptor blockers, calcium antagonists, ACE inhibitors, arteriosclerotics, antiphlogistics, anticoagulants, antihypotonics, antihypoglycaemics, antihypertensives, antifibrinolytics, antiepileptics, antiemetics, antidotes, antidiabetics, antiarrhythmics, antianaemics, antiallergics, anthelmintics, analgesics, analeptics, aldosterone antagonists, slimming agents.

Examples of cosmetic active ingredients are fragrances and aroma substances, vitamins or UV absorbers. Preferred cosmetic active ingredients are vitamins and UV absorbers, in particular UV absorbers.

Examples of UV absorbers are:
p-aminobenzoic acid derivatives, such as e.g. 2-ethylhexyl 4-dimethylaminobenzoate;
salicylic acid derivatives, such as e.g. 2-ethylhexyl salicylate;
benzophenone derivatives, such as e.g. 2-hydroxy-4-methoxybenzophenone; diethylamino hydroxybenzoyl hexyl benzoate (Uvinul A Plus) and the compound of the formula

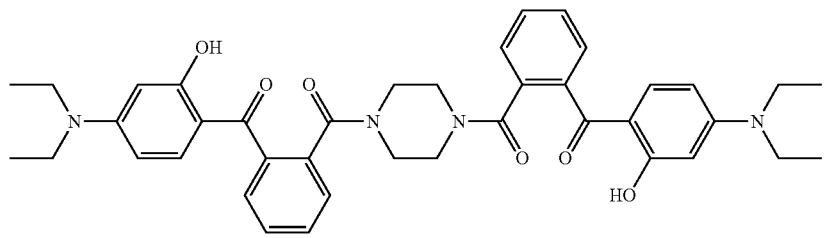 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

dibenzoylmethane derivatives, such as e.g. 1-(4-tert-bu-tylphenyl)-3-(4-methoxyphenyl)propan-1,3-dione;

diphenylacrylates, such as e.g. 2-ethylhexyl 2-cyano-3,3-diphenylacrylate and 3-(benzofuranyl)2-cyanoacrylate;

3-imidazol-4-ylacrylic acid and esters;

benzofuran derivatives, in particular 2-(p-aminophenyl) benzofuran derivatives, described in EP-A-582,189, U.S. Pat. No. 5,338,539, U.S. Pat. No. 5,518,713 and EP-A-613,893;

polymeric UV absorbers, such as e.g. the benzylidenemalonate derivatives described in EP-A-709,080;

cinnamic acid derivatives, such as e.g. the 4-methoxycinnimic acid 2-ethylhexyl ester or isoamyl ester or cinnimic acid derivatives disclosed in U.S. Pat. No. 5,601,811 and WO 97/00851;

camphor derivatives, such as e.g. 3-(4'-methyl)benzylidene-bornan-2-one, 3-benzylidene-bornan-2-one, N-[2(and 4)-2-oxyborn-3-ylidenemethyl)benzyl]acrylamide polymer, 3-(4'-trimethylammonium)benzylidene-bornan-2-one methylsulfate, 3,3'-(1,4-phenylenedimethine)-bis(7,7-dimethyl-2-oxo-bicyclo-[2.2.1]heptane-1-methanesulphonic acid) and salts, 3-(4'-sulfo)benzylidene-bornan-2-one and salts; camphor benzalkonium methosulfate;

hydroxyphenyltriazine compounds, such as e.g. 2-(4'-methoxyphenyl)-4,6-bis(2'-hydroxy-4'-n-octyloxyphenyl)-1,3,5-triazine; 2,4-bis{[4-(3-(2-propyloxy)-2-hydroxypropyloxy)-2-hydroxyl]phenyl}-6-(4-methoxyphenyl)-1,3,5-triazine; 2,4-bis{[4-(2-ethylhexyloxy)-2-hydroxyl]phenyl}-6-[4-(2-methoxyethylcarboxyl)phenylamino]-1,3,5-triazine; 2,4-bis{[4-(tris(trimethylsiloxysilylpropyloxy)-2-hydroxyl]phenyl}-6-(4-methoxyphenyl)-1,3,5-triazine; 2,4-bis{[4-(2"methylpropenyloxy)-2-hydroxyl]phenyl}-6-(4-methoxyphenyl)-1,3,5-triazine; 2,4-bis{[4-(1',1',1',3',5',5',5'-heptamethyltrisilyl-2"-methylpropyloxy)-2-hydroxy]phenyl}-6-(4-methoxyphenyl)-1,3,5-triazine; 2,4-bis{[4-(3-(2-propyloxy)-2-hydroxypropyloxy)-2-hydroxyl]phenyl}-6-[4-ethylcarboxyl)phenylamino]-1,3,5-triazine; and bis-ethylhexyloxyphenol methoxyphenyltriazine (Tinosorb S);

polyphenyl-substituted triazine compounds, such as e.g. tris-biphenyltriazine (Tinosorb A2B)

benzotriazol compounds, such as e.g. 2,2'-methylenebis (6-(2H-benzotriazol-2-yl)-4-(1,1,3,3-tetramethylbutyl) phenol

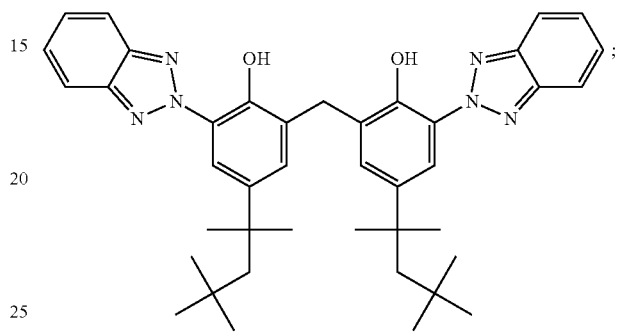

trianilino-s-triazine derivatives, such as e.g. 2,4,6-trianilino-(p-carbo-2'-ethyl-1'-oxi)-1,3,5-triazine, and also the UV absorbers disclosed in U.S. Pat. No. 5,332,568, EP-A-517,104, EP-A-507,691, WO 93/17002 and EP-A-570,838; and ethylhexyl triazone (Uvinul T 150);

2-phenylbenzimidazole-5-sulfonic acid and salts thereof;

menthyl o-aminobenzoate;

merocyanine compounds.

Preferred UV absorbers are (identified hereinbelow with INCI names): 3-BENZYLIDENE CAMPHOR, 4-METHYLBENZYLIDENE CAMPHOR, BENZOPHENONE-10, BENZOPHENONE-1, BENZOPHENONE-2, BENZOPHENONE-3, BENZOPHENONE-4, BENZOPHENONE-6, BENZOPHENONE-8, BENZYLIDENE CAMPHOR SULFONIC ACID, BUTYL METHOXYDIBENZOYLMETHANE, CAMPHOR BENZALKONIUM METHOSULFATE, CINOXATE, DEA-METHOXYCINNAMATE, DIISOPROPYL METHYL CINNAMATE, DIPROPYLENE GLYCOL SALICYLATE, ETHYL DIHYDROXYPROPYL PABA, ETHYL DIISOPROPYLCINNAMATE, ETHYL METHOXYCINNAMATE, GLYCERYL OCTANOATE DIMETHOXYCINNAMATE, GLYCERYL PABA, HOMOSALATE, ISOAMYL p-METHOXYCINNAMATE, ISOPROPYL DIBENZOYLMETHANE, ISOPROPYL METHOXYCINNAMATE, LAWSONE, MENTHYL ANTHRANILATE, MENTHYL SALICYLATE, OCTOCRYLENE, ETHYLHEXYL DIMETHYL PABA, ETHYLHEXYL METHOXYCINNAMATE, ETHYLHEXYL SALICYLATE, ETHYLHEXYL TRIAZONE, PABA, PEG-25 PABA, PENTYL DIMETHYL PABA, POLYACRYLAMIDOMETHYL BENZYLIDENE CAMPHOR, TEA-SALICYLATE, TITANIUM DIOXIDE, DIGALLOYL TRIOLEATE, ZINC OXIDE, Methylene bis-benzotriazolyl tetramethylbutylphenol, Bis-ethylhexyloxyphenol methoxyphenyltriazine, Diethylamino Hydroxybenzoyl Hexyl Benzoate, Tris-Biphenyl Triazine, BISIMIDAZYLATE, DIETHYLHEXYL BUTAMIDO TRIAZONE, DROMETRIZOLE TRISILOXANE, BENZYLIDENE MALONATE POLYSILOXANE.

The aforementioned UV absorbers can be used in mixtures with one another. Such mixtures can be used to increase the UV absorption and/or the photostability.

Examples of fragrances and aroma substances are described in WO 01/49817, or in "Flavors and Fragrances", Ullmann's Encyclopedia of Industrial Chemistry, Wiley-VCH, 2002, to which reference is expressly made.

Examples of vitamins are vitamins, provitamins and vitamin precursors from the groups A, C, E and F, in particular 3,4-didehydroretinol, beta-carotine (provitamin of vitamin A), ascorbic acid (vitamin C) and also the palmitic acid esters, glucosides or phosphates of ascorbic acid, tocopherols, in particular alpha-tocopherol, and also its esters, e.g. the acetate, the nicotinate, the phosphate and the succinate; also vitamin F, which is understood to include essential fatty acids, in particular linoleic acid, linolenic acid and arachidonic acid. A further suitable vitamin is coenzyme Q10 (ubichinone-10).

The term agrochemical active ingredients (also called pesticides hereinbelow) refers to at least one active ingredient selected from the group of fungicides, insecticides, nematicides, herbicides, safeners and/or growth regulators. Preferred pesticides are fungicides, insecticides and herbicides, in particular insecticides. Mixtures of pesticides of two or more of the aforementioned classes can also be used. The person skilled in the art is familiar with such pesticides, which can be found, for example, in the Pesticide Manual, 15th Ed. (2011), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and also insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof. Suitable fungicides are fungicides of the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolcarboxamides, guanidines, hydroxy(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides of the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolincarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

The oil is soluble in water at 20° C. to at most 20 g/l. Preferably the oil is soluble in water to at most 5 g/l, particularly preferably to at most 1 g/l.

The oil has in most cases a boiling point of at least 80° C., preferably of at least 100° C. and in particular of at least 150° C.

Suitable oils are, for example, aliphatics, aromatics (also called aromatic hydrocarbon), waxes, vegetable oils, esters and amides of vegetable oils, silicone oils, alkyl alkanoates, fatty acid amides, acetals, or dialkyl esters of an alkyldioic acid. Mixtures of these oils are likewise possible. Preferred oils are aromatics or dialkyl esters of an alkyldioic acid.

Examples of vegetable oils, esters and amides of vegetable oils are rapeseed oil, soya oil, palm oil, sunflower oil, corn seed oil, linseed oil, colza oil, olive oil, cottonseed oil, rapeseed oil methyl ester, rapeseed oil ethyl ester, colza oil methyl ester, colza oil ethyl ester, almond oil, jojoba oil, orange oil, wheat germ oil, peach kernel oil, the liquid fractions of coconut oil, and also mixtures of vegetable oils and/or esters and amides thereof.

Examples of aromatics are benzene, toluene, xylene, naphthaline, biphenyl, o- or m-terphenyl, mono- or poly-$C_1$-$C_{20}$-alkyl-substituted aromatic hydrocarbons, such as dodecylbenzene, tetradecylbenzene, hexadecylbenzene, methylnaphthaline, diisopropylnaphthaline, hexylnaphthaline or decylnaphthaline. Also suitable are technical-grade aromatic mixtures in the boiling range from 30 to 250° C., and also mixtures of the aforementioned aromatics. Preferred aromatics are technical-grade aromatic mixtures in the boiling range from 30 to 250° C.

Examples of aliphatics are saturated or unsaturated $C_{10}$-$C_{40}$-hydrocarbons, which are branched or preferably linear e.g. such as n-tetradecane, n-pentadecane, n-hexadecane, n-heptadecane, n-octadecane, n-nonadecane, n-eicosane, n-heneicosane, n-docosane, n-tricosane, n-tetracosane, n-pentacosane, n-hexacosane, n-heptacosane, n-octacosane, cyclic hydrocarbons, e.g. cyclohexane, cyclooctane, cyclodecane, mineral oils comprising saturated hydrocarbons, or high-pressure-hydrogenated mineral oil (so-called white oils). Also suitable are mixtures of the aforementioned aliphatics. Preferred aliphatics are mineral oils.

Examples of waxes are natural and synthetic waxes, such as montanic acid waxes, montanic ester waxes, carnauba wax, polyethylene wax, oxidized waxes, polyvinyl ether waxes, ethylene vinyl acetate wax and mixtures of the aforementioned waxes. Preference is given to low-melting waxes, in particular those which are liquid at 30 to 100° C., in particular at 35 to 70° C.

Examples of alkyl alkanoates are $C_1$-$C_{40}$-alkyl esters of $C_2$-$C_{40}$-alkanoic acids, preferably $C_1$-$C_{40}$-alkyl esters of $C_8$-$C_{40}$-alkanoic acids or $C_6$-$C_{40}$-alkyl esters of $C_2$-$C_{40}$-alkanoic acids. The alkyl group or the alkanoic acid can optionally be functionalized with double bonds and/or hydroxy groups. Ethylhexyl lactate, inter alia, is suitable.

Further examples of alkyl alkanoates are esters of linear $C_6$-$C_{24}$-fatty acids with linear $C_3$-$C_{24}$-alcohols, esters of branched $C_6$-$C_{13}$-carboxylic acids with linear $C_6$-$C_{24}$-fatty alcohols, esters of linear $C_6$-$C_{24}$-fatty acids with branched alcohols, in particular 2-ethylhexanol, esters of hydroxycarboxylic acids with linear or branched $C_6$-$C_{22}$-fatty alcohols, in particular dioctyl malate, esters of linear and/or branched fatty acids with polyhydric alcohols (such as e.g. propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{24}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups. Monoesters of the fatty acids with alcohols having 3 to 24 carbon atoms are also of importance. This substance group is the product of the esterification of fatty acids having 8 to 24 carbon atoms, such as, for example, caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachic acid, gadoleic acid, behenic acid and erucic acid, and technical-grade mixtures thereof which are produced e.g. during the pressurized cleavage of natural fats and oils, during the reduction of aldehydes from the Roelen oxo synthesis or the dimerization of unsaturated fatty acids, with alcohols such as, for example, isopropyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachyl alcohol, gadoleyl alcohol, behenyl alcohol, erucyl alcohol and brassidyl alcohol, and also technical-grade mixtures thereof which are produced e.g. during the high-pressure hydrogenation of technical-grade methyl esters based on fats and oils or aldehydes from the Roelen oxosynthesis, and also as monomer fraction during the dimerization of unsaturated fatty alcohols.

Examples of fatty acid amides are N,N-di-$C_1$-$C_{12}$-alkyl-$C_8$-$C_{22}$-alkylamides, such as N,N-dimethyldecanamide, or N,N-dimethyldodecanamide.

Examples of dialkyl esters of an alkyldioic acid are di-$C_2$-$C_{32}$-alkyl esters of $C_4$-$C_{32}$-alkyldioic acids, preferably di-$C_2$-$C_{18}$-alkyl esters of $C_6$-$C_{16}$-alkyldioic acids. Of particular suitability are succinic acid dibutyl ester, adipic acid dibutyl ester and phthalic acid dibutyl ester, with adipic acid dibutyl ester being particularly good.

Examples of fatty alcohols are Guerbet alcohols based on fatty alcohols having 6 to 18, preferably 8 to 10, carbon atoms.

Examples of fatty carbonates are linear and branched $C_6$-$C_{22}$-fatty alcohol carbonates and Guerbet carbonates.

Examples of dialkyl ethers are linear or branched, symmetrical or asymmetrical dialkyl ethers having in total between 12 and 36 carbon atoms, in particular 12 to 24 carbon atoms, such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methylpentyl n-octyl ether.

Examples of acetals are aromatic acetals, such as those of the formula (A)

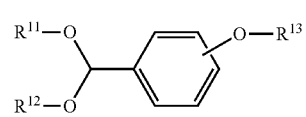

(A)

where $R^{11}$ and $R^{12}$, independently of one another, are $C_1$-$C_{20}$-alkyl or together are a $C_2$-$C_{14}$-alkylene, and $R^{13}$ is $C_1$-$C_{20}$-alkyl. Preferably, $R^{11}$ and $R^{12}$, independently of one another, are $C_1$-$C_4$-alkyl or together a $C_2$-$C_6$-alkylene. Particularly preferably, $R^{11}$, $R^{12}$ and $R^{13}$ are methyl.

The ionic liquid comprises a cation and an anion. Usually, the stoichiometric composition of anion and cation is selected such that the charges are neutralized. Ionic liquids per se and their preparation are generally known.

The ionic liquid is in most cases soluble in oil. The oil solubility can be determined, for example, at 20° C. in Cetiol® B (dibutyl adipate) as oil. The ionic liquid is preferably soluble to at least 0.05% by weight, particularly preferably to at least 0.1% by weight, particularly preferably to at least 1% by weight, and in particular to at least 10% by weight, in Cetiol® B.

The melting point of the ionic liquid is in most cases below 220° C., preferably below 150° C., particularly preferably below 100° C., and in particular below 30° C. The ionic liquid can comprise a plurality of different anions or different cations.

Suitable cations comprise an ammonium of the formula (I)

$N^+R^1R^2R^3R^4$ (I)

and $R^1$, $R^2$, $R^3$ and $R^4$, independently of one another, are alkyl radicals which can be substituted with heterofunctional groups, and which can form aliphatic ring systems among one another. Preferably, $R^1$, $R^2$, $R^3$ and $R^4$, independently of one another, are alkyl and/or hydroxyalkyl. Particularly preferably, $R^1$, $R^2$, $R^3$ and $R^4$, independently of one another, are $C_1$-$C_{20}$ alkyl and/or $C_1$-$C_{20}$ hydroxyalkyl. Very particularly preferably, $R^1$, $R^2$, $R^3$ and $R^4$, independently of one another, are $C_1$-$C_8$ alkyl and/or $C_1$-$C_8$ hydroxyalkyl. Examples are tetrabutylammonium (TBA) or cholinium (N,N,N-trimethyl-N-hydroxyethylammonium).

In a further form, $R^1$, $R^2$, $R^3$ and $R^4$, independently of one another, are alkyl radicals which may be substituted with heterofunctional groups, and which form aliphatic ring systems among one another. Examples are N,N-di-$C_1$-$C_{12}$-pyrrolidinium, 5-azaspiro[4.4]nonane, or N,N-dimethylpyrrolidinium.

Suitable cations further comprise an imidazolium of the formula (II)

(II)

where $R^5$ is hydrogen or alkyl, $R^6$ is alkyl, and $R^7$ is hydrogen or alkyl. An alkyl radical consists of carbon and hydrogen. It is free from functional groups. The alkyl radical may be linear, cyclic or branched. Preferably, $R^5$ is hydrogen or $C_1$-$C_{20}$ alkyl, $R^6$ is $C_1$-$C_{20}$ alkyl, and $R^7$ is H or $C_1$-$C_{20}$ alkyl. Particularly preferably, $R^5$ is hydrogen or $C_1$-$C_6$ alkyl, $R^6$ is $C_1$-$C_6$ alkyl, and $R^7$ is H or $C_1$-$C_6$ alkyl. $R^7$ is preferably H or methyl, in particular H. Examples are N-ethyl-N'-methylimidazolium (EMIM), N-methylimidazolium (MEHIM), N-butyl-N'-methylimidazolium (BMIM), N-ethyl-N'-ethylimidazolium (EEIM), N-n-propyl—N'—N-propylimidazolium (PPIM).

Suitable cations also comprise an N-substituted pyridinium derivative, such as N-alkylpyridinium, where the alkyl radical is preferably a $C_1$-$C_{12}$-alkyl radical, in particular a $C_1$-$C_6$-alkyl radical.

Suitable cations also comprise an N,N'-disubstituted pyrazolium derivative, such as an N,N'-dialkylpyrazolium derivative, where the alkyl radical is preferably a $C_1$-$C_{12}$-alkyl radical, in particular a $C_1$-$C_6$-alkyl radical. The dialkylpyrazolium derivative can optionally be substituted with $C_1$-$C_4$-alkyl, such as 1,2,5-trimethylpyrazolium.

Suitable cations also comprise a guanidinium derivative, such as guanidinium, hexamethylguanidinium, arginine cation, or creatinium.

Preferred cations are ammonium of the formula (I) and imidazolium of the formula (II).

Suitable anions are all customary anions for ionic liquids. For example, the anion comprises a carboxylate, sulfonate, sulfate, phosphonate, phosphate, halogen, bis(trifluorosulfonyl)imide, aluminum tetrachloride, phosphorus fluoride (such as phosphorus hexafluoride), or dicyanimide, and also mixtures thereof. Preferred anions are carboxylates, sulfates, alkylsulfonates, halides (such as iodide or chloride), phosphonates, phosphates, bis(trifluorosulfonyl)imide, or dicyanimide (also known as 2-cyanoguanidine), and mixtures thereof. Preferred anions are carboxylates and alkylsulfonates. Particularly preferred anions are alkyl carboxylates, polyether-containing carboxylates, and alkylsulfonates. In a further particularly preferred form, the anions are alkylcarboxylates. In a further particularly preferred form, the anions are polyether-containing carboxylates. In a further particularly preferred form, the anions are alkylsulfonates.

Suitable carboxylates are a $C_1$-$C_{30}$ alkylcarboxylate, $C_1$-$C_{20}$ hydroxyalkylcarboxylate, a polyether-containing carboxylate, arylcarboxylates and polycarboxylates, and mixtures thereof. Preferred carboxylates are $C_1$-$C_{30}$ alkylcarboxylate, $C_1$-$C_{20}$ hydroxyalkylcarboxylate, and polyether-containing carboxylate.

Preferred alkylcarboxylate is a $C_2$-$C_{32}$ alkylcarboxylate, such as acetate, propionate, hexanoate, 2-ethylhexanoate, heptanoate, octanoate, isononanoate, decanoate, laurate, oleic acid, palmitic acid, stearate, or octadecanoate.

Preferred hydroxyalkylcarboxylate is $C_2$-$C_6$ hydroxyalkylcarboxylate, such as glycolate, gluconate, glucoheptonate, glucuronate, glyceric acid, lactic acid, lactobionic acid, mevalonate.

Example of polyether-containing carboxylates are disclosed in WO 2008/135482, page 5, line 25 to page 6, line 20. Preferred polyether-containing carboxylate has the formula (III)

$(R^aO(CH_2CH_2O)_nCH_2CO_2^-)$ (III)

where n has a value from 0 to 3 and $R^a$ is a $C_1$-$C_8$-alkyl or an acetate radical; or of the formula (IV)

$R^b—O—CH_2CO_2^-$ (IV)

where $R^b$ is a $C_1$-$C_{18}$-alkyl. $R^b$ is preferably $C_3$-$C_{12}$-alkyl, in particular hexyl.

Particular preference is given to a polyether-containing carboxylate of the formula (III), where n has a value of 2 and $R^a$ is a methyl (i.e. [2-(2-methoxyethoxy)ethoxy]acetate).

Preferred polycarboxylates are aliphatic di- and tricarboxylates having 2 to 32 carbon atoms, such as aconitic acid, adipic acid, aspartic acid, citric acid, fumaric acid, galactaric acid, glutamic acid, glutaric acid, oxoglutaric acid, maleic acid, malic acid, malonic acid, oxalate, sebacic acid, succinic acid, tartaric acid.

Preferred arylcarboxylates are benzoic acid, cinnimic acid, hippuric acid.

Suitable alkylsulfonates are $C_1$-$C_{20}$ alkylsulfonates, in particular $C_1$-$C_{10}$ alkylsulfonates, and mixtures thereof. Examples are ethanesulfonate or octanesulfonate.

Suitable sulfates are those of the formula $R^c$—$OSO_3^-$, where $R^c$ is $C_1$-$C_{18}$-alkyl or $C_6$-$C_{12}$-aryl, preferably $C_1$-$C_8$-alkyl or $C_6$-aryl, and mixtures thereof.

Suitable phosphates are $C_1$-$C_{10}$-dialkylphosphates, where the two alkyl radicals may be identical or different, and mixtures thereof. Preference is given to dimethylphosphate or dibutylphosphate.

Suitable halides are chloride, bromide or iodide, preferably chloride.

Particularly suitable ionic liquids are tetrabutylammonium[2-(2-methoxyethoxy)ethoxy]acetate, N-ethyl-N'-methylimidazolium acetate, N-ethyl-N'-methylimidazolium isononanoate, N-ethyl-N'-methylimidazolium octanoate, N-ethyl-N'-methylimidazolium dibutylphosphate, N-butyl-N'-methylimidazolium acetate, N-ethyl-N'-ethylimidazolium propionate, N-propyl-N'-propylimidazolium acetate, cholinium octanoate, tetrabutylammonium stearate.

The ionic liquids can be prepared by known processes. Examples have been described by Wasserscheid and Welton, Ionic liquids in synthesis, 2nd edition, 2007, Wiley-VCH, or WO 2008/135482.

The composition usually comprises 0.5 to 90% by weight of ionic liquid, based on the total amount of active ingredient, oil and ionic liquid. Preferably, it comprises 1 to 80% by weight, particularly preferably 1 to 40% by weight, and in particular 1 to 15% by weight, of ionic liquid. In a further form, the composition can comprise up to 35% by weight, preferably up to 20% by weight, particularly preferably up to 10% by weight, very particularly preferably up to 5% by weight and in particular up to 3% by weight, of ionic liquid, based on the total amount of active ingredient, oil and ionic liquid.

The weight ratio of oil to ionic liquid is usually in the range from 1000/1 to 1/100. Preferably, the weight ratio of oil to ionic liquid is in the range from 100/1 to 1/1, in particular in the range from 50/1 to 3/1.

The composition usually comprises at least 1% by weight of active ingredient. Preferably, it comprises at least 10% by weight, in particular at least 20% by weight, of active ingredient, based on the total amount of the composition. The composition can comprise up to 60% by weight, preferably up to 50% by weight, of active ingredient.

The composition can be present in the form of a solution or as a dispersion (in which case preferably the oil and the ionic liquid can be present in two separate phases). The active ingredient here can be dissolved in the oil, in the ionic liquid, or in both. In a preferred form, the composition is in the form of a solution. In a further preferred form, the composition is in the form of a dispersion.

The composition is usually in the form of a concentrate, which can comprise up to 10% by weight, preferably up to 5% by weight and in particular up to 1% by weight, of water.

The composition can be diluted with water in order, in so doing, to obtain an aqueous dispersion comprising the composition according to the invention. For example, for agrochemical applications, prior to the application, water is added to the composition in order to obtain a sprayable, aqueous dispersion. The aqueous dispersion can comprise at least 10% by weight of water, preferably at least 20% by weight, and in particular at least 40% by weight, of water. The aqueous dispersion can be an aqueous suspension, aqueous emulsion or aqueous suspoemulsion. Preferably, the dispersion is an aqueous emulsion.

The invention further relates to a process for the preparation of the liquid composition according to the invention, in which the active ingredient, the oil and the ionic liquid are brought into contact. For this, the components can be mixed in any desired order. The process can take place at temperatures from 5 to 100° C.

The composition according to the invention (especially when the organic active ingredient is an agrochemical active ingredient) can comprise formulation auxiliaries, in particular agrochemical formulation auxiliaries. Suitable formulation auxiliaries are solvents, liquid carriers, solid carriers or fillers, surfactants, dispersants, emulsifiers, wetting agents, adjuvants, solubility promoters, penetration promoters, protective colloids, stickers, thickeners, humectants, repellants, attractants, feed stimulants, compatibilizing agents, bactericides, antifreezes, foam inhibitors, colorants, adhesives and binders, wherein surfactants are preferred.

Suitable surfactants are surface-active compounds, such as anionic, cationic, nonionic and amphoteric surfactants, block polymers, polyelectrolytes and mixtures thereof. Such surfactants can be used as emulsifier, dispersant, solubility promoter, wetting agent, penetration promoter, protective colloid or auxiliary. Examples of surfactants can be found in McCutcheon's, Volume 1: Emulsifiers & Detergents, McCutcheon's Directories, Glen Rock, USA, 2008 (International edition or North American edition). Preferred surfactants are nonionic and anionic surfactants.

The composition according to the invention can comprise any desired amounts of surfactant. It can comprise 0.1 to 40% by weight, preferably 1 to 30 and in particular 2 to 20% by weight total amount of surfactants (e.g. nonionic surfactant and optionally anionic surfactant), based on the total amount of the composition.

Suitable anionic surfactants are alkali metal, alkaline earth metal or ammonium salts of sulfonates, sulfates, phosphates, carboxylates and mixtures thereof. Examples of sulfonates are alkylarylsulfonates, diphenylsulfonates, alpha-olefin sulfonates, lignosulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols or of fatty acid esters. Examples of phosphates are phosphate esters. Examples of carboxylates are alkylcarboxylates and also carboxylated alcohol or alkylphenol ethoxylates. Preferred anionic surfactants comprise sulfates or sulfonates.

Suitable nonionic surfactants are alkoxylates, N-substituted fatty acid amides, amine oxides, esters, surfactants based on sugar, polymeric surfactants and mixtures thereof. Examples of alkoxylates are compounds such as alcohols, alkylphenols, amines, amides, arylphenols, fatty acids or fatty acid esters which have been alkoxylated with 1 to 100 (preferably 1 to 50) equivalents. For the alkoxylation, ethylene oxide and/or propylene oxide can be used, preferably ethylene oxide. Examples of N-substituted fatty acid amides are fatty acid glucamides or fatty acid alkanolamides. Examples of esters are fatty acid esters, glycerol esters or monoglycerides. Examples of surfactants based on sugar are sorbitans, ethoxylated sorbitans, sucrose and glucose esters or alkylpolyglucosides. Examples of polymeric surfactants are homo- or copolymers of vinylpyrrolidone, vinyl alcohols or vinyl acetate. Preferred nonionic surfactants comprise alkoxylates.

Suitable cationic surfactants are quaternary surfactants, e.g. quaternary ammonium compounds with one or two hydrophobic groups, or salts of long-chain primary amines. Suitable amphoteric surfactants are alkylbetains and imidazolines. Suitable block polymers are block polymers of the A-B- or A-B-A type comprising polyethylene oxide and polypropylene oxide blocks, or of the A-B-C type comprising alkanol, polyethylene oxide and polypropylene oxide. Suitable polyelectrolytes are polyacids or polybases. Examples of polyacids are alkali metal salts of polyacrylic acid or polyacid comb polymers. Examples of polybases are polyvinylamines or polyethyleneamines.

Suitable adjuvants are compounds which themselves have a negligibly small or even no pesticidal effectiveness and which improve the biological effect of compound I on the target. Examples are surfactants, mineral or vegetable oils and other auxiliaries. Further examples can be found in Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates and silicates.

Suitable bactericides are bronopol and isothiazoline derivatives such as alkylisothiazolinones and benzisothiazolinones.

Suitable antifreezes are ethylene glycol, propylene glycol, urea and glycerol.

Suitable foam inhibitors are silicones, long-chain alcohols and salts of fatty acids.

Suitable dyes (e.g. in red, blue or green) are pigments which are poorly soluble in water, and water-soluble dyes. Examples are inorganic colorants (e.g. iron oxide, titanium oxide, iron hexacyanoferrate) and organic colorants (e.g. alizarin, azo and phthalocyanine colorants).

Suitable stickers or binders are polyvinylpyrrolidones, polyvinyl acetates, polyvinyl alcohols, polyacrylates, biological or synthetic waxes and cellulose ethers.

In a preferred form the composition comprises at least one surfactant. In a more preferred form the organic active ingredient is an agrochemical active ingredient and the composition comprises at least one surfactant.

Preferably, the surfactant comprises at least one nonionic surfactant (such as one, two or three nonionic surfactants) and optionally an anionic surfactant. More preferably, the surfactant comprises at least one nonionic surfactant selected from alkoxylates (such as alcohols, fatty acids or fatty acid esters which have been alkoxylated with at least one equivalent (preferably from 2 to 100 equivalents) of ethylene oxide) and optionally an anionic surfactant selected from sulfates or sulfonates.

In one preferred form the surfactant comprises at least two nonionic surfactants, such as at least two alkoxylates. More preferably, the surfactant comprises an alkoxylate A which has been alkoxylated with at least 20 (preferably at least 30, and in particular at least 40) equivalents of ethylene oxide. Even more preferably, the surfactant comprises an alkoxylate A which has been alkoxylated with at least 20 (preferably at least 30, and in particular at least 40) equivalents of ethylene oxide, and an alkoxylate B which has been alkoxylated with up to 20 (preferably up to 15 and in particular up to 10) equivalents of ethylene oxide. The weight ratio of alkoxylate A to alkoxylate B may be from 1:10 to 10:1, preferably from 1:5 to 5:1, and in particular from 1:3 to 3:1.

In a preferred embodiment, the active ingredient is a cosmetic active ingredient and the compositions according to the invention are present in the form of a cosmetic formulation. Examples are creams, shampoo, hair spray, lotion. The preparation and further formulation auxiliaries are known to the person skilled in the art.

The cosmetic formulations, such as, for example, creams, gels, lotions, alcoholic and aqueous/alcoholic solutions, emulsions, wax/fat masses, stick preparations, powders or ointments, can also comprise, as further auxiliaries and additives, mild surfactants, superfatting agents, pearlescent waxes, consistency regulators, thickeners, polymers, silicone compounds, fats, waxes, stabilizers, deodorant active ingredients, antidandruff agents, film formers, swelling agents, further UV absorbers, antioxidants, hydrotropes, preservatives, insect repellants, self-tanning agents, solubilizers, perfume oils, dyes, antimicrobial agents and the like.

Superfatting agents which can be used are substances such as, for example, lanolin and lecithin, and polyethoxylated or acrylated lanolin and lecithin derivatives, polyol fatty acid esters, monoglycerides and fatty acid alkanolamides, the latter simultaneously serving as foam stabilizers.

Suitable pearlescent waxes are, for example: alkylene glycol esters, specifically ethylene glycol distearate; fatty acid alkanolamides, specifically coconut fatty acid diethanolamide; partial glycerides, specifically stearic acid monoglyceride; esters of polyhydric, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, specifically laurone and distearyl ether; fatty acid such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Suitable consistency regulators are primarily fatty alcohols or hydroxy fatty alcohols having 12 to 22 and preferably 16 to 18 carbon atoms, and also partial glycerides, fatty acids and hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar-guar, agar-agar, alginates and tyloses, carboxymethylcellulose and hydroxymethylcellulose, also relatively high molecular weight polyethylene glycol mono- and diesters of fatty acids, polyacrylates (e.g. Carbopole® from Goodrich or Synthalene® from Sigma), polyacrylamides, polyvinyl alcohol and polyvinylpyrrolidone, surfactants, such as, for example, ethoxylated fatty acid glycerides, esters of fatty acids with polyols such as, for example, pentaerythritol or trimethylolpropane, fatty alcohol ethoxylates with a narrowed homolog distribution or alkyl oligoglucosides, and electrolytes such as sodium chloride or ammonium chloride.

Suitable silicone compounds are, for example dimethylpolysiloxanes, methylphenyl-polysiloxanes, cyclic silicones, and amino-, fatty acid-, alcohol-, polyether-, epoxy-, fluorine-, glycoside- and/or alkyl-modified silicone compounds, which may be present at room temperature either as a liquid or in resin form. Also suitable are simethicones, which are mixtures of dimethicones having an average chain length from 200 to 300 dimethylsiloxane units and hydrogenated silicates. A detailed overview of suitable volatile silicones can be found, moreover, by Todd et al. in Cosm. Toil. 91, 27 (1976).

Suitable deodorant active ingredients are e.g. antiperspirants such as, for example, aluminum chlorohydrates (cf. J. Soc. Cosm. Chem. 24, 281 (1973)). Commercially available under the trade name Locron® from Hoechst AG, Frankfurt (FRG) is, for example, an aluminum chlorohydrate which corresponds to the formula $Al_2(OH)_5Cl \times 2.5H_2O$ and whose use is particularly preferred (cf. J. Pharm. Pharmacol. 26, 531 (1975)). As well as the chlorohydrates, aluminum hydroxylacetates and also acidic aluminum/zirconium salts can also be used. Esterase inhibitors can be added as further deodorant active ingredients. These are preferably trialkyl citrates such as trimethyl citrate, tripropyl citrate, triisopropyl citrate, tributyl citrate and in particular triethyl citrate (Hydagen® CAT, Henkel KGaA, Dusseldorf/FRG). The substances inhibit the enzyme activity and, as a result, reduce the odor formation. Further substances which are suitable as esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, such as, for example, citric acid, malic acid, tartaric acid or tartaric acid diethyl ester. Antibacterial active ingredients, which influence the germ flora and kill perspiration-decomposing bacteria and/or inhibit their growth, can likewise be present in the preparations (in particular in the stick preparations). Examples thereof are chitosan, phenoxyethanol and chlorhexidine gluconate. 5-chloro-2-(2,4-dichlorophenoxy)phenol has proven to be particularly effective (Irgasan®, Ciba Specialty Chemicals Inc.).

Antidandruff agents which can be used are e.g. climbazole, octopirox and zinc pyrethione. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid or salts thereof and similar compounds. Swelling agents which can be used for aqueous phases are montmorillonites, clay mineral substances, pemulen and alkyl-modified carbopol grades (Goodrich). Further suitable polymers and/or swelling agents can be found in the overview by R. Lochhead ?? Cosm. Toil. 108, 95 (1993).

Besides the primary photoprotective substances, it is also possible to use secondary photoprotective agents of the antioxidant type, which interrupt the photochemical reaction chain which is triggered when UV radiation penetrates into the skin or hair. Typical examples of such antioxidants are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. ?-carotene, ?-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxine, glutathione, cysteine, cystine, cystamine and the glycosyl, N-acetyl, methyl, ethyl, propyl, amyl, butyl and lauryl, palmitoyl, oleyl, ?-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to ?mol/kg), also (metal) chelating agents (e.g. ?-hydroxy fatty acids, palmitic acid, phytic acid, lactoferrin), ?-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. ?-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (e.g. vitamin-A palmitate), and coniferyl benzoate of benzoin resin, rutinic acid and derivatives thereof, ?-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl) propionyl]sulfanilic acid (and salts thereof, such as e.g. the sodium salts), zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients. In addition, HALS (="Hindered Amine Light Stabilizers") compounds may also be mentioned. The fraction of antioxidants here is usually between 0.001 and 30% by weight, preferably 0.01 to 3% by weight, based on the weight of the UV absorber(s).

To improve the flow behavior, hydrotropes, such as, for example, ethanol, isopropyl alcohol or polyols, can also be used. Polyols which are suitable here have preferably 2 to 15 carbon atoms and at least two hydroxyl groups. The polyols can also comprise further functional groups, in particular amino groups, and/or be modified with nitrogen. Typical examples are:
  glycerol;
  alkylene glycols, such as, for example, ethylene glycol, diethylene glycol, propylene glycol, butylene glycol, hexylene glycol, and polyethylene glycols having an average molecular weight of from 100 to 1000 Daltons;
  technical-grade oligoglycerol mixtures with a degree of self-condensation of 1.5 to 10 such as, for example, technical-grade diglycerol mixtures with a diglycerol content of from 40 to 50% by weight;
  methylol compounds, such as, in particular, trimethylol ethane, trimethylol propane, trimethylol butane, pentaerythritol and dipentaerythritol;
  lower alkyl glucosides, in particular those having 1 to 8 carbon atoms in the alkyl radical, such as, for example, methyl and butyl glucoside;
  sugar alcohols having 5 to 12 carbon atoms, such as, for example, sorbitol or mannitol;
  sugars having 5 to 12 carbon atoms, such as, for example, glucose or sucrose;
  amino sugars, such as, for example, glucamine;
  dialcohol amines, such as diethanolamine or 2-amino-1, 3-propanediol.

Suitable preservatives are, for example, phenoxyethanol, formaldehyde solution, parabens, pentanediol or sorbic acid, and also the other substance classes listed in Annex 6, part A and B of the Cosmetics Ordinance.

Perfume oils which may be mentioned are mixtures of natural and/or synthetic fragrances. Natural fragrances are e.g. extracts from flowers (lily, lavender, rose, jasmine, neroli, ylang-ylang), stems and leaves (geranium, patchouli, petitgrain), fruits (anise, coriander, cumin, juniper), fruit peels (bergamot, lemon, orange), roots (mace, angelica, celery, cardamom, costus, iris, calmus), woods (pinewood, sandalwood, guaiac wood, cedar wood, rosewood), herbs and grasses (tarragon, lemongrass, sage, thyme), needles and branches (spruce, fir, pine, dwarf pine), resins and balsams (galbanum, elemi, benzoe, myrrh, olibanum, opoponax). Also suitable are animal raw materials such as, for example, civet and castoreum. Typical synthetic fragrances are e.g. products of the ester, ether, aldehyde, ketone, alcohol and hydrocarbon type.

Fragrance compounds of the ester type are e.g. benzyl acetate, phenoxyethyl isobutyrate, p-tert-butyl cyclohexylacetate, linalyl acetate, dimethyl benzyl carbinyl acetate, phenylethyl acetate, linalyl benzoate, benzyl formate, ethylmethyl phenyl glycinate, allyl cyclohexyl propionate, styrallyl propionate and benzyl salicylate. The ethers include, for example, benzyl ethyl ether; the aldehydes e.g. the linear alkanals having 8 to 18 carbon atoms, citral, citronellal, citronellyl oxyacetaldehyde, cyclamen aldehyde, hydroxycitronellal, lilial and bourgeonal; the ketones e.g. the ionones, ??isomethylionone and methyl cedryl ketone; the alcohols e.g. anethole, citronellol, eugenol, isoeugenol, geraniol, linalool, phenylethyl alcohol and terpineol; the hydrocarbons include primarily the terpenes and balsams. However, preference is given to using mixtures of different fragrances which together produce a pleasing scent note. Essential oils of relatively low volatility, which in most cases are used as aroma components, are also suitable as perfume oils. e.g. sage oil, camomile oil, clove oil, melissa oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, hexylcinnaldehyde, geraniol, benzyl acetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, ?-damascone, geranium oil bourbon, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat, alone or in mixtures.

Dyes which can be used are the substances approved and suitable for cosmetic purposes, as are listed, for example, in the publication "Kosmetische Farbemittel" [Cosmetic Colorants] from the Dyes Commission of the German Research Society, Verlag Chemie, Weinheim, 1984, pages 81 to 106. The dyes are usually used in concentrations of from 0.001 to 0.1% by weight, based on the total mixture.

Typical examples of antimicrobial agents are preservatives with a specific effect against Gram-positive bacteria, such as, for example, 2,4,4'-trichloro-2'-hydroxydiphenyl ether, chlorhexidine (1,6-di(4-chlorophenylbiguanido) hexane) or TCC (3,4,4'-trichlorocarbanilide). Numerous fragrances and essential oils also have antimicrobial properties. Typical examples are the active ingredients eugenol, menthol and thymol in clove oil, mint oil and thyme oil. An interesting natural deodorant is the terpene alcohol farnesol (3,7,11-trimethyl-2,6,10-dodecatrien-1-ol) which is present in linden blossom oil. Glycerol monolaurate has already proven useful as a bacteriostatic. Usually, the fraction of additional antimicrobial agents is 0.1 to 2% by weight, based on the solids fraction of the preparation.

Furthermore, the cosmetic compositions can comprise, as auxiliaries, antifoams, such as silicones, structurants, such as maleic acid, solubility promoters, such as ethylene glycol, propylene glycol, glycerol or diethylene glycol, opacifiers, such as latex, styrene/PVP or styrene/acrylamide copolymers, complexing agents, such as EDTA, NTA, alanine diacetic acid or phosphonic acids, propellants, such as propane-butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or ?-mercaptoethanesulfonic acid, or oxidizing agents, such as hydrogen peroxide, potassium bromate or sodium bromate.

Suitable insect repellents are e.g. N,N-diethyl-m-toluamide, 1,2-pentanediol or insect repellant 3535; suitable self-tanning agents are e.g. dihydroxyacetone, erythrulose or mixtures of dihydroxyacetone and erythrulose.

The cosmetic formulation include a very wide variety of cosmetic compositions. In particular, the following compositions are e.g. suitable:

Compositions for skin care, such as e.g. skin washing and cleaning compositions in the form of bar or liquid soaps, syndets or washing pastes, Bathing preparations, such as e.g. liquid (foam baths, milks, shower preparations) or solid bathing preparations, such as e.g. bathing tablets and bathing salts;

Skin care compositions, such as e.g. skin emulsions, multiple emulsions or skin oils;

Decorative body care compositions, such as e.g. face make-ups in the form of day or powder creams, face powders (loose and pressed), blusher or cream make-ups, eye care compositions, such as e.g. eye shadow preparations, mascara, eyeliner, eye creams or eye-fix creams; lip care compositions, such as e.g. lipstick, lip gloss, lip liner pencil, nail care compositions, such as nail varnish, nail varnish remover, nail hardeners, or cuticle removers;

Foot care compositions, such as e.g. foot baths, foot powders, foot creams and foot balsams, specifically deodorants and antiperspirants or callus-removing compositions;

Photoprotective compositions, such as sun milks, lotions, creams, oils, sun blocks or tropicals, pre-tanning preparations or after-sun preparations;

Skin-tanning compositions, such as e.g. self-tanning creams;

Depigmentation compositions, such as e.g. preparations for bleaching skin or compositions for lightening skin;

Insect-repelling compositions ("repellants"), such as e.g. insect oils, lotions, sprays or sticks;

Deodorants, such as deodorant sprays, pump sprays, deodorant gels, sticks or roll-ons;

Antiperspirants, such as e.g. antiperspirant sticks, creams or roll-ons;

Compositions for the cleansing and care of blemished skin, such as e.g. syndets (solid or liquid), peeling or scrub preparations or peeling masks;

Hair removal compositions in chemical form (depilation), such as e.g. hair removal powders, liquid depilatories, creamy or pasty depilatories, depilatories in gel form or aerosol foams;

Shaving compositions, such as e.g. shaving soap, foaming shaving creams, non-foaming shaving creams, foams, gels, pre-shave preparations for dry shaving, aftershaves or aftershave lotions;

Scented compositions, such as e.g. scented waters (eau de cologne, eau de toilette, eau de parfum, parfum de toilette, perfume), perfume oils or perfume creams;

Cosmetic compositions for treating hair, such as e.g. hair washing compositions in the form of shampoos, hair conditioners, hair care compositions, such as e.g. pre-treatment compositions, hair tonics, styling creams, styling gels, pomades, hair rinses, treatment packs, intensive hair treatments, compositions for shaping the hair, such as e.g. waving compositions for producing permanent waves (hot wave, mild wave, cold wave), hair-smoothing preparations, liquid hair-setting compositions, hair foams, hairsprays, bleaching compositions, such as e.g. hydrogen peroxide solutions, lightening shampoos, bleaching creams, bleaching powders, bleaching slurries or oils, temporary, semi-permanent or permanent hair colorants, preparations with self-oxidizing dyes, or natural hair colorants such as henna or camomile.

These listed end formulations can be present in a wide variety of presentation forms, such as e.g.

in the form of liquid preparations as a W/O, O/W, O/W/O, W/O/W, PIT and all types of microemulsions, in the form of a gel, in the form of an oil, a cream, milk or lotion, in the form of a powder, a lacquer, a tablet or make-up, in the form of a stick, in the form of a spray (spray with propellant gas or pump spray) or an aerosol, in the form of a foam, or in the form of a paste.

Of particular importance as cosmetic compositions for the skin here are photoprotective compositions such as sun milks, lotions, creams, oils, sun blocks or tropicals, pre-tanning preparations or after-sun preparations; also skin-tanning compositions, such as e.g. self-tanning creams. Of particular interest here are sunscreen creams, sunscreen lotions, sun protection oils, sunscreen milk, and also sunscreen preparations in the form of a spray.

Of particular importance as cosmetic compositions for hair here are the aforementioned compositions for treating hair, in particular hair washing compositions in the form of shampoos, hair conditioners, hair care compositions, such as e.g. pre-treatment compositions, hair tonics, styling creams, styling gels, pomades, hair rinses, treatment packs, intensive hair treatments, hair-smoothing preparations, liquid hair-setting compositions, hair foams and hairsprays. Of particular interest here are hair washing compositions in the form of shampoos. A shampoo has e.g. the following composition: 0.01 to 5% by weight of one of the UV absorbers according to the invention, 12.0% by weight of sodium laureth-2-sulfate, 4.0% by weight of cocamidopropyl betaine, 3.0% by weight of NaCl and water ad 100%.

In a preferred embodiment, the active ingredient is a pesticide and the compositions according to the invention are in the form of an agrochemical formulation. The agrochemical formulation is in most cases diluted prior to application in order to prepare the so-called tank mix. For the dilution, mineral oil fractions of medium to high boiling point, such as kerosene or diesel oil, also coal tar oils, and oils of vegetable or animal origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, isophorone, strong polar solvents, e.g. dimethyl sulfoxide, N-methylpyrrolidone or water are suitable. Preference is given to using water. It is also possible to only add the amphiphilic agent to the tank mix. In this embodiment, the composition according to the invention is in the form of a tank mix.

The diluted composition is usually used for spraying or fogging. Oils of various types, wetting agents, adjuvants, herbicides, bactericides, fungicides can be added to the tank mix directly prior to application (tank mix). These compositions can be added to the compositions according to the invention in the weight ratio 1:100 to 100:1, preferably 1:10 to 10:1. The pesticide concentration in the tank mix can be varied within relatively large ranges. In general, it is between 0.0001 and 10%, preferably between 0.01 and 1%. The application rates for application in crop protection are between 0.01 and 2.0 kg of active ingredient per ha, depending on the type of desired effect.

The use of the agrochemical formulations is possible for controlling phytopathogenic fungi and/or undesired plant growth and/or undesired insect or mite attack and/or for regulating the growth of plants, where the composition is allowed to act on the particular pests, their habitat or the plants to be protected from the respective pest, the soil and/or on undesired plants and/or the useful plants and/or their habitat. Furthermore, the use of the agrochemical formulations is possible for controlling undesired insect or mite attack on plants and/or for controlling phytopathogenic fungi and/or for controlling undesired plant growth, in which case seed materials of useful plants are treated with the composition.

The invention further relates to the use of the ionic liquid for increasing the solubility of the active ingredient in the oil. Suitable and preferred embodiments, such as the oil, the ionic liquid and the active ingredient, are as described above. The solubility can be increased by at least 10%, preferably by 30%, particularly preferably by 100% and in particular by 500%, in each case based on the solubility in pure oil. In a further form, the solubility of the active ingredient is increased by 10%, preferably by 30%, particularly preferably by 100% and in particular by 500%, in each case based on the linearly interpolated solubility in the respective mixture of oil and ionic liquid. The linearly interpolated solubility is determined theoretically by a linear joining line between the solubility of the active ingredient in pure oil and in pure ionic liquid.

Advantages of the invention are that high concentrations of active ingredient can be brought into solution; that the composition is only slightly toxic; that the active ingredient is not chemically degraded by the ionic liquid; that the ionic liquid can only be prepared easily, that it has a high agrochemical effect, that very high concentrations of active ingredient can be brought into solution, that ionic liquids that are solid at room temperature can be used, that the compositions are only of low viscosity, that, for the same concentration of active ingredient, less organic solvent or oil needs to be added to the composition, and that organic solvents can be replaced by oils, in particular vegetable oils, esters of vegetable oils or amides of vegetable oils.

The examples below illustrate the invention without limiting it.

EXAMPLES

Cetiol® B: Cosmetic oil of bibutyl adipate, commercially available from BASF SE.
Fluxapyroxad: Fungicide, 3-(difluoromethyl)-1-methyl-N-(3',4',5'-trifluorobiphenyl-2-yl)pyrazole-4-carboxamide.
Uvinul® T150: 2,4,6-trianilino-p-(carbo-2'-ethylhexyl-1'-oxy)-1,3,5-triazine; CAS No. 88122-99-0, commercially available from BASF SE.
Tinosorb® S: bis-ethylhexyloxyphenol methoxyphenyl triazine (also known as bemotrizinol).
Surf A: Ethoxylated Castor oil (~40 EO)
Surf B: Polyoxyl 40 Hydrogenated Castor Oil
Surf C: Ethoxylated Tristyrylphenols
Surf D: Ethoxylated Polyarylphenolsulphate Ammonium Salz
Surf E: C10-Guerbet-alcohol Ethoxy-late (7 EO)
Surf F: C10-Guerbet-alcohol Ethoxylate (3 EO)
Surf G C13C15-oxoalcohol Ethoxylat (3 EO)
Surf H: iso C12Alkylbenzene sulfonate Ca— salt
Surf I: C13-Oxoalkohol-ethoxylate (+3EO)
Surf J: C13-Oxoalkohol-ethoxylate (+7EO)
Surf K: C13-Oxoalkohol-ethoxylate (+10EO)
Surf L: C13-Oxoalkohol-ethoxylate (+12EO)
Surf M: C10C18-Alkohol-ethoxylate (+5EO)

Example 1

Increased Solubility of Agrochemical Active Ingredient

The solubility was tested at 21° C. For this, increasing amounts of active ingredient were added stepwise to oil (Cetiol® B or Solvesso®), which comprised the ionic liquid, until the maximum solubility was reached. Alternatively, the oil, which comprised the ionic liquid, was saturated with the active ingredient and the soluble fraction of active ingredient was quantified by means of HPLC.

The results are summarized in tables 1 to 3. In the first line of the tables, in each case the weight ratios of oil to IL are given.

TABLE 1

Solubility [g/l] of fluxapyroxad with Cetiol ® B as oil.

| Ionic liquid (IL) | 100 Oil | 90/10 Oil/IL | 80/20 Oil/IL | 60/40 Oil/IL | 20/80 Oil/IL | 100 IL |
|---|---|---|---|---|---|---|
| Tetrabutylammonium octadecanoate | 3.0 | 15.3 | — | 35.5 | 45.9 | 5.0 |
| N-ethyl-N'-methylimidazolium isononanoate | 3.0 | 20.7 | — | 46.7 | 48.7 | 9.5 |

TABLE 1-continued

Solubility [g/l] of fluxapyroxad with Cetiol ® B as oil.

| Ionic liquid (IL) | 100 Oil | 90/10 Oil/IL | 80/20 Oil/IL | 60/40 Oil/IL | 20/80 Oil/IL | 100 IL |
|---|---|---|---|---|---|---|
| Tetrabutylammonium [2-(2-methoxyethoxy)ethoxy]acetate | 3.0 | 16 | 27.5 | 40.8 | 38.3 | 9.5 |
| N-butyl-N'-methylimidazolium acetate | 3.0 | 23.7 | — | 50.6 | 54.9 | 42.4 |
| N-ethyl-N'-methylimidazolium acetate | 3.0 | 25.6 | — | 54.9 | 56.2 | 47.2 |
| N-ethyl-N'-ethylimidazolium propionate | 3.0 | 24.2 | — | 50.8 | 60.2 | 45.7 |
| N-butyl-N'-methylimidazolium dimethylphosphate | 3.0 | — | 29 | 43.1 | 44.1 | 5 |
| N-ethyl-N'-methylimidazolium dibutylphosphate | 3.0 | — | 31.1 | 46.0 | 16.8 | 9.5 |
| N-ethyl-N'-methylimidazolium heptanoate | 3.0 | — | 35.9 | 50 | 28.4 | 26.9 |
| N-ethyl-N'-methylimidazolium octanoate | 3.0 | — | 34.3 | 49.5 | 25.7 | 20.8 |
| N-propyl-N'-propylimidazolium acetate | 3.0 | — | 35.4 | 49.6 | 59.2 | 36.7 |
| Cholinium octanoate | 3.0 | — | 20.8 | 33.6 | 34.2 | 5 |

TABLE 2

Solubility [g/l] of fluxapyroxad with Solvesso ® 200 ND as oil

| Ionic liquid (IL) | 100 Oil | 90/10 Oil/IL | 60/40 Oil/IL | 20/80 Oil/IL | 100 IL |
|---|---|---|---|---|---|
| Tetrabutylammonium octadecanoate | 1.5 | 14.5 | 33.3 | 35.5 | 5 |
| N-ethyl-N'-methylimidazolium isononanoate | 1.5 | 15.3 | 42.9 | 28.6 | 9.5 |
| Tetrabutylammonium [2-(2-methoxyethoxy)ethoxy]acetate | 1.5 | 18.4 | — | — | 9.5 |
| N-ethyl-N'-ethylimidazolium propionate | 1.5 | 21.3 | 50.5 | 39.4 | 45.7 |

TABLE 3

Solubility [g/l] of fluxapyroxad with Agnique AMD 12 ® (N,N-dimethyldodecanamide, lauryl N,N-dimethylamide) as oil

| Ionic liquid (IL) | 100 Oil | 90/10 Oil/IL | 60/40 Oil/IL | 20/80 Oil/IL | 100 IL |
|---|---|---|---|---|---|
| Tetrabutylammonium octadecanoate | 21.0 | 25.9 | 39.1 | 40.7 | 5 |
| N-ethyl-N'-methylimidazolium isononanoate | 21.0 | 32 | 48.1 | 38.4 | 9.5 |
| N-butyl-N'-methylimidazolium acetate | 21.0 | 36 | 55.9 | 43.1 | 1 |
| N-ethyl-N'-methylimidazolium acetate | 21.0 | 38.2 | 40.4 | 39.5 | 1 |
| Tetrabutylammonium [2-(2-methoxyethoxy)ethoxy]acetate | 21.0 | 29.7 | 33.1 | 37.5 | 9.5 |

TABLE 4

Solubility [g/l] of Uvinul ® T150 with Cetiol ® B as oil

| Ionic liquid (IL) | 100 Oil | 90/10 Oil/IL | 60/40 Oil/IL | 20/80 Oil/IL | 100 IL |
|---|---|---|---|---|---|
| Tetrabutylammonium octadecanoate | 14.2 | 28.6 | 39.4 | — | 1 |
| N-ethyl-N'-methylimidazolium isononanoate | 14.2 | 32.4 | 45.7 | 34.8 | 1 |
| N-butyl-N'-methylimidazolium acetate | 14.2 | 37.5 | 54.1 | 41.5 | 5 |
| N-ethyl-N'-methylimidazolium acetate | 14.2 | 37.5 | 52.8 | 40.8 | 1 |
| N-ethyl-N'-ethylimidazolium propionate | 14.2 | 33.3 | 54.3 | 44.1 | 5 |
| Cholinium [2-(2-methoxyethoxy)ethoxy]acetate | 14.2 | 21.3 | — | — | 1 |

TABLE 5

Solubility [g/l] of Tinosorb ® S with Cetiol ® B as oil

| Ionic liquid (IL) | 100 Oil | 90/10 Oil/IL | 60/40 Oil/IL | 20/80 Oil/IL | 100 IL |
|---|---|---|---|---|---|
| N-ethyl-N'-methylimidazolium isononanoate | 6.2 | 13.8 | 22.4 | 19.2 | 9.5 |
| N-butyl-N'-methylimidazolium acetate | 6.2 | 11.7 | 14.3 | 12.4 | 1 |
| N-ethyl-N'-ethylimidazolium heptanoate | 6.2 | 13 | 21.9 | — | 1 |
| N-ethyl-N'-ethylimidazolium octanoate | 6.2 | 13 | 21.9 | 16.7 | 1 |

Example 2

Increased Solubility of UV Absorber

The solubilities were determined as in example 1 and the results were summarized in table 4 and 5.

Example 3

Aqueous Dilutions

A mixture of 8 wt % N-butyl-N'-methylimidazolium (BMIM) acetat, 20 wt % Fluxapyroxad, 72 wt % Cetiol® B, and the surfactant as listed in the Table 6 were prepared. The mixture was diluted at room temperature with water in a weight ratio of 1 part of the mixture to 100 parts water yielding a homogenous dispersion.

TABLE 6 composition of mixtures (in wt %)

| Surfactant 1 | Conc. 1 | Surfactant 2 | Conc. 2 | Surfactant 3 | Conc. 3 |
|---|---|---|---|---|---|
| Surf A | 8 | | | | |
| Surf A | 3.8 | Surf I | 10.4 | | |
| Surf A | 4.2 | Surf I | 10.4 | Surf E | 2.5 |
| Surf A | 3.8 | Surf F | 10.5 | | |
| Surf A | 3.8 | Surf G | 10.5 | | |
| Surf B | 6 | Surf I | 8.3 | | |
| Surf C | 5.9 | Surf H | 8.2 | | |
| Surf C | 5.8 | Surf H | 8.4 | Surf E | 2.7 |
| Surf D | 12.7 | Surf I | 4.4 | | |
| Surf D | 8.1 | Surf I | 8.4 | | |
| Surf D | 4 | Surf I | 12.6 | | |

TABLE 7

Composition of mixtures (in wt %)

| Surfactant 1 | Conc. 1 | Surfactant 2 | Conc. 2 | Ratio |
|---|---|---|---|---|
| Surf A | 4.1 | Surf I | 10.2 | 2.5 |
| Surf A | 5.2 | Surf I | 10.6 | 2 |
| Surf A | 8.1 | Surf I | 8 | 1 |
| Surf A | 10.4 | Surf I | 5.4 | 0.5 |
| Surf A | 10.7 | Surf I | 4.5 | 0.4 |

TABLE 8

Composition of mixtures (in wt %)

| Surfactant 1 | Conc. 1 | Surfactant 2 | Conc. 2 | Surfactant 3 | Conc. 3 |
|---|---|---|---|---|---|
| Surf A | 4.7 | Surf I | 12.4 | Surf E | 3 |
| Surf A | 4.5 | Surf I | 10.6 | Surf E | 3.6 |
| Surf A | 4.6 | Surf I | 10.4 | Surf E | 4.9 |
| Surf A | 4.5 | Surf I | 10.3 | Surf E | 5.9 |

TABLE 9

Composition of mixtures (in wt %)

| Surfactant 1 | Conc. 1 | Surfactant 2 | Conc. 2 | Surfactant 3 | Conc. 3 |
|---|---|---|---|---|---|
| Surf A | 4.7 | Surf I | 12.4 | Surf E | 3 |
| Surf A | 4.3 | Surf I | 10.5 | Lutensol TO7 | 3.2 |
| Surf A | 4.5 | Surf I | 10.6 | Surf K | 3.3 |
| Surf A | 4.2 | Surf I | 10.2 | Surf L | 3.4 |
| Surf A | 4 | Surf I | 10.2 | Surf M | 3.4 |

Example 4

Aqueous Dilutions

A mixture of 9 wt % cholinium octanoate, 10 wt % Fluxapyroxad, 81 wt % Cetiol® B, and the surfactant as listed in the Table 6 were prepared. The mixture was diluted at room temperature with water in a weight ratio of 1 part of the mixture to 100 parts water yielding a homogenous dispersion.

TABLE 10

Composition of mixtures (in wt %)

| Surfactant 1 | Conc. 1 | Surfactant 2 | Conc. 2 | Surfactant 3 | Conc. 3 |
|---|---|---|---|---|---|
| Surf A | 4.4 | Surf I | 10.7 | | |
| Surf A | 4.2 | Surf I | 10.5 | Surf E | 1.8 |
| Surf D | 12 | Surf I | 4 | | |
| Surf D | 12 | Surf I | 4 | Surf E | 3 |

Example 5

Aqueous Dilutions

A mixture of 8.5 wt % N-ethyl-N'-methylimidazolium (EMIM) acetate, 15 wt % Fluxapyroxad, 76.5 wt % Cetiol® B, and the surfactant as listed in the Table 6 were prepared. The mixture was diluted at room temperature with water in a weight ratio of 1 part of the mixture to 100 parts water yielding a homogenous dispersion.

TABLE 11

Composition of mixtures (in wt %)

| Surfactant 1 | Conc. 1 | Surfactant 2 | Conc. 2 | Surfactant 3 | Conc. 3 |
|---|---|---|---|---|---|
| Surf A | 4.4 | Surf I | 10.7 | | |
| Surf A | 4.2 | Surf I | 10.6 | Surf E | 2 |
| Surf D | 12 | Surf I | 4 | | |
| Surf D | 12 | Surf I | 4 | Surf E | 3 |

Example 6

Aqueous Dilutions

A mixture of 8 wt % N-ethyl-N'-methylimidazolium (EMIM) octanoate, 20 wt % Fluxapyroxad, 72 wt % Cetiol® B, and the surfactant as listed in the Table 6 were prepared. The mixture was diluted at room temperature with water in a weight ratio of 1 part of the mixture to 100 parts water yielding a homogenous dispersion.

TABLE 12

Composition of mixtures (in wt %)

| Surfactant 1 | Conc. 1 | Surfactant 2 | Conc. 2 | Surfactant 3 | Conc. 3 |
|---|---|---|---|---|---|
| Surf A | 4.3 | Surf I | 10.6 | | |
| Surf A | 4.3 | Surf I | 10.4 | Surf E | 2 |
| Surf D | 12 | Surf I | 4 | | |
| Surf D | 12 | Surf I | 4 | Surf E | 3 |

The invention claimed is:
1. A liquid composition comprising:
A) an organic active ingredient in dissolved form, which is soluble in water at 20° C. to at most 10 g/l and is soluble in di butyl adipate at 20° C. to at most 10% by weight, wherein the active ingredient is a UV absorber selected from the group consisting of 2-(4'-methoxyphenyl)-4,6-bis(2'-hydroxy-4'-n-octyloxyphenyl)-1,3,5-triazine, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxyl)phenylarmino]-1,3,5 -triazine, 2,4-bis{[4-(tris(trimethylsiloxysilylpropyloxy)-2-hydroxy]phenyl}-6-

(4-methoxyphenyl)-1,3,5-triazine, 2,4-bis{[4-(2"methylpropenyloxy)-2-hydroxy]phenyl}-6-(4-methoxyphenyl)-1,3,5-triazine, 2,4-bis{[4-( 1',1',1',3',5',5 ',5'-heptamethyltrisilyl-2"-methylpropyloxy)-2-hydroxy] phenyl}-6-(4-methoxyphenyl)-1,3,5-triazine, 2,4-bis {[4-(3  -(2-propyloxy)-2-hydroxypropyloxy)-2-hydroxy]phenyl}-6-[4-ethylcarboxyl)phenylamino]-1,3,5-triazine, bis-ethylhexyloxyphenol methoxyphenyltriazine, tris-biphenyltriazine, and 2,4,6-trianilino-(p-carbo-2'-ethylhexyl-1'-oxy)-1,3,5-triazine;

B) an oil that is soluble in water at 20° C. to at most 20 g/l, the oil selected from an aromatic hydrocarbon, an alkyl alkanoate, a fatty acid amide, or a dialkyl ester of an alkyldioic acid; and C) an ionic liquid comprising a cation and an anion, where the cation is selected from: an ammonium of the formula (I)

N⁺R¹R²R³ R⁴     (I)

and $R^1$, $R^2$, $R^3$ and $R^4$, independently of one another, are $C_1$-$C_{20}$ alkyl or $C_1$-$C_{20}$ hydroxyalkyl; or an imidazolium of the formula (II)

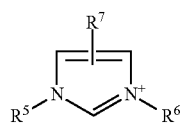
(II)

and $R^5$ is hydrogen or $C_1$-$C_{20}$ alkyl, $R^6$ is $C_1$-$C_{20}$ alkyl, and $R^7$ is $C_1$-$C_{20}$ alkyl.

2. The composition according to claim 1, where the cation is the imidazolium of the formula (II), and $R^5$ is hydrogen or $C_1$-$C_6$ alkyl, $R^6$ is $C_1$-$C_6$ alkyl, and $R^7$ is hydrogen, and the anion is an alkyl carboxylate, polyether-containing carboxylate, or alkysulfonate.

3. The composition according to claim 1, where a weight ratio of the oil to the ionic liquid is in the range from 50:1 to 3:1, and the concentration of the UV absorber is from 1% to 10% by weight.

4. The composition according to claim 1, where the cation is the ammonium of the formula (I), and the anion is an alkyl carboxylate, polyether-containing carboxylate, or alkylsulfonate.

5. The composition according to claim 1, further comprising from 1 to 25% by weight of at least one surfactant.

6. The composition according to claim 5, where the surfactant comprises at least one nonionic surfactant selected from alkoxylates and optionally an anionic surfactant selected from sulfates.

7. The composition according to claim 1, where the anion is selected from a carboxylate, sulfonate, sulfate, phosphonate, phosphate, halogen, bis(trifluorosulfonyl)imide, aluminum tetrachloride, phosphorus fluoride, or dicyanimide.

8. The composition according to claim 1, where the anion is an alkyl carboxylate, polyether-containing carboxylate, or alkylsulfonate.

9. The composition according to claim 1, where the composition is a solution or dispersion, and comprises at most 5% by weight of water.

10. The composition according to claim 1, where the composition is a dispersion and comprises at least 5% by weight of water.

11. The composition according to claim 1, where the composition is a cosmetic.

12. The composition according to claim 1, where the active ingredient is soluble in water at 20° C. to at most 3 g/l and is soluble in dibutyl adipate at 20° C. to at most 3% by weight.

13. The composition according to claim 12, where the oil is soluble in water at 20° C. to at most 5 g/l.

14. The composition according to claim 11, where the oil is an ester or amide of a vegetable oil selected from the group consisting of rapeseed oil, soya oil, palm oil, sunflower oil, corn seed oil, linseed oil, colza oil, olive oil, cottonseed oil, rapeseed oil methyl ester, rapeseed oil ethyl ester, colza oil methyl ester, colza oil ethyl ester, almond oil, jojoba oil, orange oil, wheat germ oil, peach kernel oil, the liquid fractions of coconut oil, and any one mixture mixtures thereof.

15. The composition according to claim 1, where the ionic liquid has a melting point less than 30° C.

16. The composition according to claim 15, wherein, $R^1$, $R^2$, $R^3$ and $R^4$, are independently of one another selected from $C_1$-$C_8$ alkyl or $C_1$-$C_8$ hydroxyalkyl.

17. The composition according to claim 3, wherein the UV absorber is selected from 2,4,6-trianilino-p-(carbo-2'-ethylhexyl-1'-oxy)-1,3,5-triazine or bis-ethylhexyloxyphenol methoxyphenyl triazine.

* * * * *